US009801649B2

(12) United States Patent
Akagane et al.

(10) Patent No.: US 9,801,649 B2
(45) Date of Patent: Oct. 31, 2017

(54) TREATMENT DEVICE, TREATMENT DEVICE UNIT AND TREATMENT SYSTEM

(71) Applicant: OLYMPUS CORPORATION, Tokyo (JP)

(72) Inventors: Tsunetaka Akagane, Hachioji (JP); Yoshitaka Honda, Hachioji (JP); Tsuyoshi Hayashida, Hachioji (JP); Tadashi Kitayama, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/139,230

(22) Filed: Apr. 26, 2016

(65) Prior Publication Data
US 2016/0235432 A1 Aug. 18, 2016

Related U.S. Application Data

(63) Continuation of application No. PCT/JP2014/083015, filed on Dec. 12, 2014.

(30) Foreign Application Priority Data

Dec. 13, 2013 (JP) ................................ 2013-258522

(51) Int. Cl.
*A61B 17/32* (2006.01)
*A61B 18/14* (2006.01)
(Continued)

(52) U.S. Cl.
CPC .. *A61B 17/320092* (2013.01); *A61B 18/1442* (2013.01); *A61B 17/320068* (2013.01);
(Continued)

(58) Field of Classification Search
CPC ........... A61B 17/320068; A61B 2017/320072; A61B 2017/320076; A61B 2017/320088; A61B 17/320092; A61F 9/00745
See application file for complete search history.

(56) References Cited

U.S. PATENT DOCUMENTS 6,193,709 B1   2/2001  Miyawaki et al.
2009/0264909 A1* 10/2009 Beaupre ......... A61B 17/320092
                                                    606/169

(Continued)

FOREIGN PATENT DOCUMENTS

JP    7-154982 A    6/1995
JP    2000-33092 A    2/2000
(Continued)

OTHER PUBLICATIONS

Mar. 17, 2015 International Search Report issued in International Patent Application No. PCT/JP2014/083015.
(Continued)

*Primary Examiner* — Diane Yabut
(74) *Attorney, Agent, or Firm* — Oliff PLC

(57) ABSTRACT

A treatment device includes a probe having a treatment portion to treat a biological tissue by using the ultrasonic vibration generated in an ultrasonic transducer; an action portion being able to be close to and away from the treatment portion and including a pressing portion that presses the biological tissue to the treatment portion; and a vibration damping portion disposed in a part of the pressing portion in a state of facing the treatment portion, moving following the treatment portion to which the ultrasonic vibration is transmitted when abutting on the treatment portion in a state where the ultrasonic vibration is transmitted to the treatment portion, and prevented from being grinded by the treatment portion to which the ultrasonic vibration is transmitted.

14 Claims, 11 Drawing Sheets

(51) Int. Cl.
 *A61F 9/007* (2006.01)
 *A61B 17/00* (2006.01)
 *A61B 17/28* (2006.01)

(52) U.S. Cl.
 CPC . *A61B 18/1445* (2013.01); *A61B 2017/00026* (2013.01); *A61B 2017/00106* (2013.01); *A61B 2017/2825* (2013.01); *A61B 2017/320072* (2013.01); *A61B 2017/320076* (2013.01); *A61B 2017/320088* (2013.01); *A61F 9/00745* (2013.01)

(56) References Cited

U.S. PATENT DOCUMENTS

| | | | |
|---|---|---|---|
| 2009/0270853 A1* | 10/2009 | Yachi | A61B 17/320092 606/27 |
| 2010/0036405 A1 | 2/2010 | Giordano et al. | |
| 2010/0063527 A1 | 3/2010 | Beaupr | |
| 2014/0135804 A1* | 5/2014 | Weisenburgh, II | A61B 17/320092 606/169 |
| 2015/0164531 A1* | 6/2015 | Faller | A61B 17/320092 606/169 |

FOREIGN PATENT DOCUMENTS

| | | |
|---|---|---|
| JP | 2002-119518 A | 4/2002 |
| JP | 2005-102811 A | 4/2005 |
| JP | 2011-530330 A | 12/2011 |
| JP | 5259883 B2 | 8/2013 |
| WO | 2010/017149 A1 | 2/2010 |
| WO | 2013/158545 A1 | 10/2013 |

OTHER PUBLICATIONS

Jun. 23, 2016 International Preliminary Report on Patentability issued in International Patent Application No. PCT/JP2014/083015.

* cited by examiner

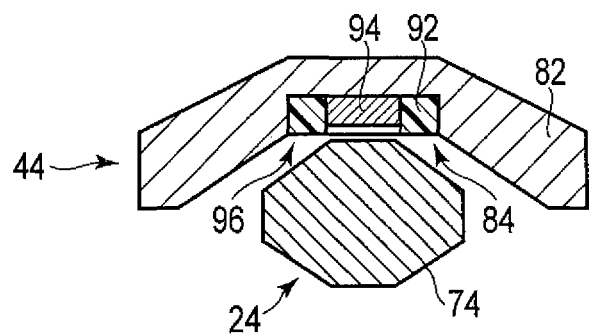
F I G. 3A
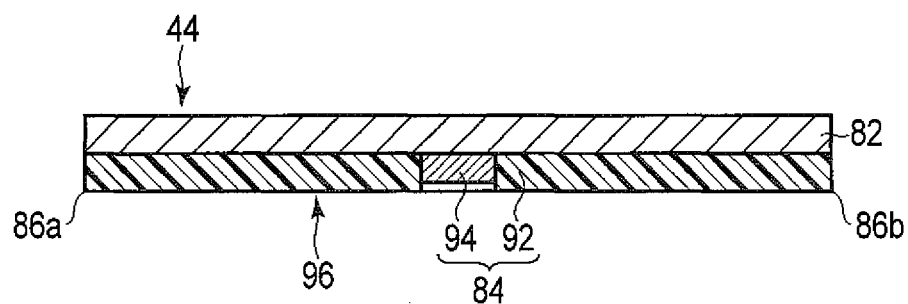
F I G. 3B
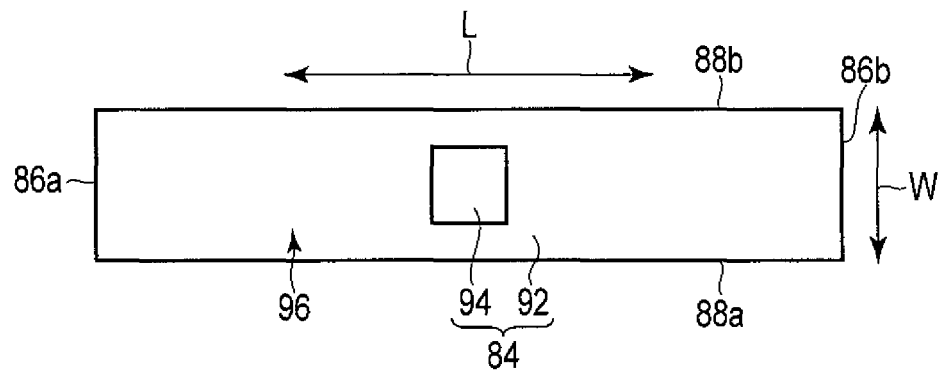
F I G. 3C

TREATMENT DEVICE, TREATMENT DEVICE UNIT AND TREATMENT SYSTEM

CROSS-REFERENCE TO RELATED APPLICATIONS

This application is a Continuation Application of PCT Application No. PCT/JP2014/083015, filed Dec. 12, 2014 and based upon and claiming the benefit of priority from prior Japanese Patent Application No. 2013-258522, filed Dec. 13, 2013, the entire contents of all of which are incorporated herein by reference.

BACKGROUND OF THE INVENTION

1. Field of the Invention

This invention relates to a treatment device, a treatment device unit and a treatment system to treat a biological tissue.

2. Background Art

For example, in Jpn. Pat. Appln. KOKAI Publication No. 2002-119518, a treatment device is disclosed in which a biological tissue is sandwiched between a treatment portion of a distal end of a probe to which an ultrasonic vibration is transmitted and a jaw operable and closable to the treatment portion to perform a treatment such as coagulation or incision of the biological tissue by the ultrasonic vibration. On a surface of the jaw which faces the treatment portion, a pad made of a resin material such as PTFE is disposed. Further, the pad abuts on the treatment portion of the probe immediately after the biological tissue is separated in the treatment portion of the probe.

In the treatment device of Jpn. Pat. Appln. KOKAI Publication No. 2002-119518, a conductive material is disposed in a jaw main body, and when the pad is worn and the probe abuts on the conductive material, a change of impedance can be detected to inform a period to replace the pad by a warning sound or the like.

BRIEF SUMMARY OF THE INVENTION

According to one embodiment of the present invention, a treatment device includes: a probe in which an ultrasonic vibration generated in an ultrasonic transducer is transmittable from a proximal portion thereof to a distal portion thereof, and which has a treatment portion disposed in the distal portion to treat a biological tissue by using the ultrasonic vibration transmitted to the distal portion; an action portion which is configured to be close to and away from the treatment portion and which includes a pressing portion that presses the biological tissue to the treatment portion; and a conductive vibration damping portion which is disposed in a part of the pressing portion in a state of facing the treatment portion, which moves following the treatment portion to which the ultrasonic vibration is transmitted when abutting on the treatment portion in a state where the ultrasonic vibration is transmitted to the treatment portion, and which is prevented from being grinded by the treatment portion to which the ultrasonic vibration is transmitted.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 3A is a schematic view of the treatment device unit of the treatment system according to the first embodiment, showing a transverse cross section of an action portion indicating a state of crossing a plate made of a vibration damping alloy material and a transverse cross section of a treatment portion of a probe;

FIG. 3B is a schematic view of the treatment device unit of the treatment system according to the first embodiment, showing a longitudinal cross section of the action portion indicating the state of crossing the plate made of the vibration damping alloy material;

FIG. 3C is a schematic front view of the treatment device unit of the treatment system according to the first embodiment, showing a grasping portion in which the plate made of the vibration damping alloy material is substantially disposed in a center in a longitudinal direction and a width direction;

DETAILED DESCRIPTION OF THE INVENTION

Hereinafter, embodiments of this invention will be described with reference to the drawings.

A first embodiment will be described with reference to FIG. 1 to FIG. 6B.

Figure 1:
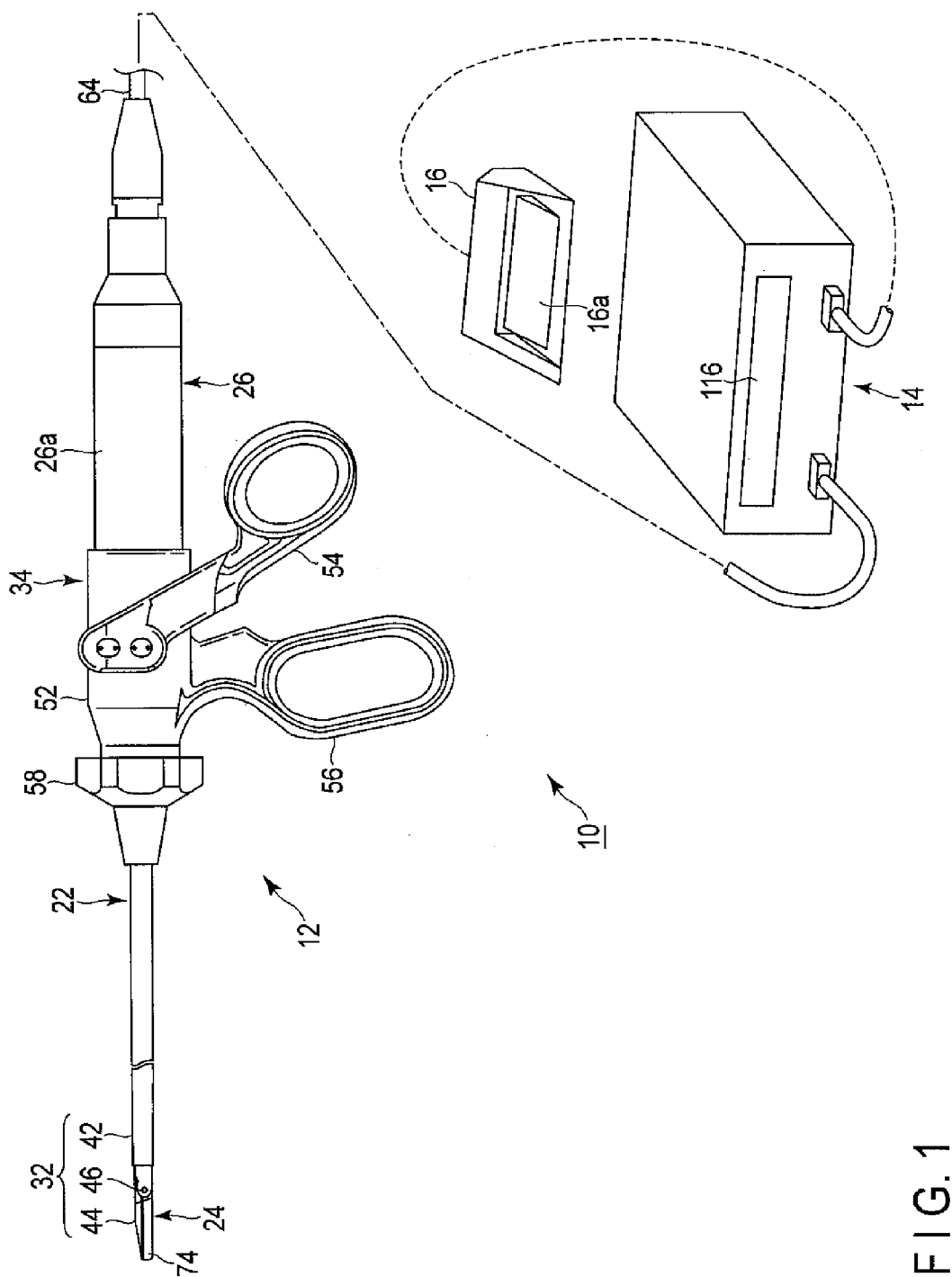
FIG. 1 is a schematic view showing a treatment system according to first and second embodiments.

As shown in FIG. 1, a treatment system 10 according to this embodiment includes a treatment device unit 12, a controller 14, and a foot switch 16. In this embodiment, there will be described an example where the controller 14 executes constant current control to maintain amplitude of an ultrasonic vibration.

Figure 2:
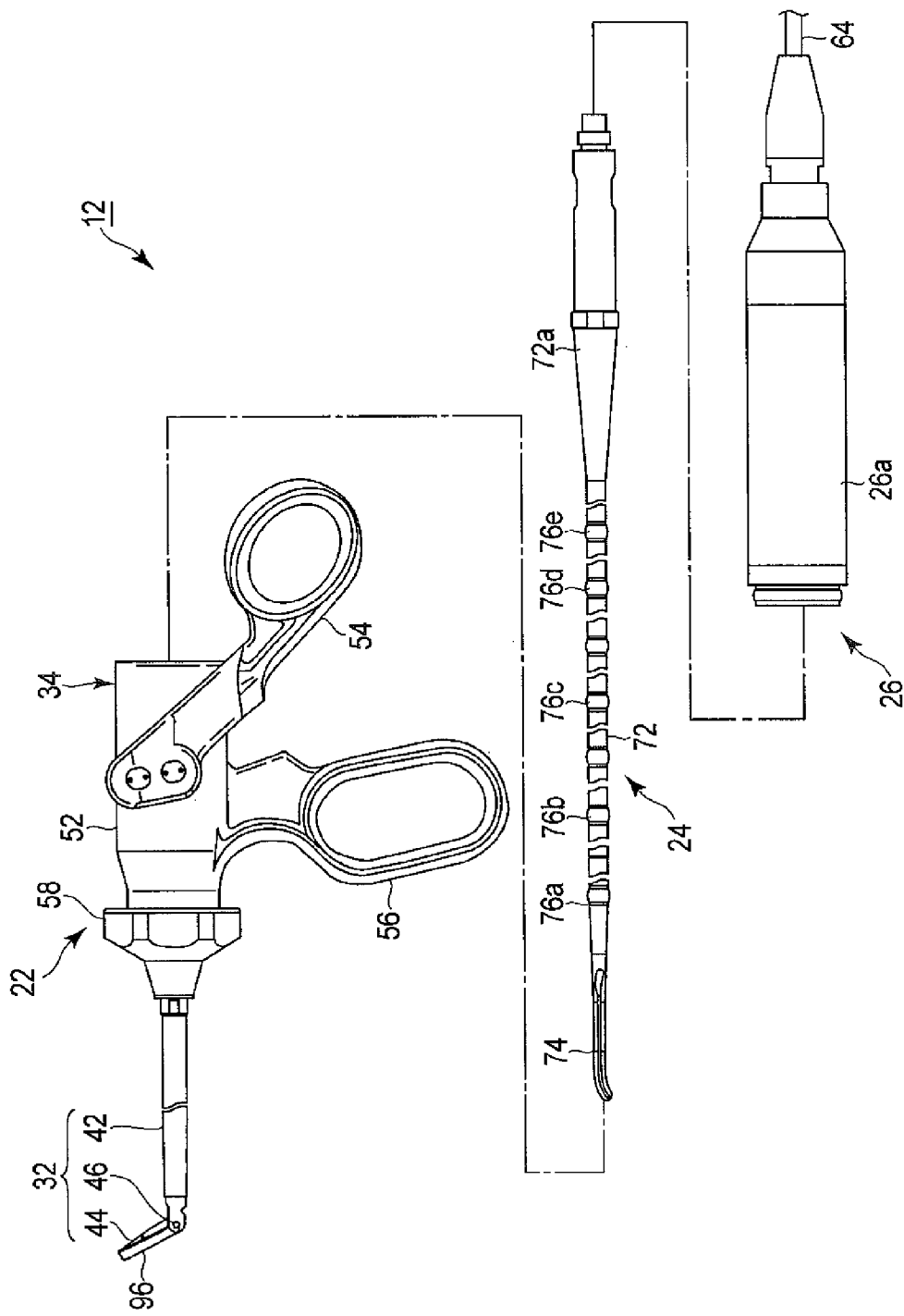
FIG. 2 is a schematic view showing an exploded state of a treatment device unit of the treatment system according to the first and second embodiments.

As shown in FIG. 1 and FIG. 2, the treatment device unit 12 includes an operation unit 22 and a probe 24 as treatment devices which can be assembled with and disassembled from each other. The probe 24 is inserted into the operation unit 22. The treatment device unit 12 further includes a vibrator unit 26. A rear end portion of the probe 24 is connected to the vibrator unit 26 in the operation unit 22.

The treatment device unit 12 is held by a user, and a biological tissue can be cut and divided by using the ultrasonic vibration generated in a vibrator 62 that will be described later. The operation unit 22 includes an insertion section 32 and an operation section 34. The insertion section 32 has an elongated sheath 42 and an action portion (a movable member) 44. The action portion 44 is disposed at a distal end of the sheath 42 and a proximal portion of the action portion 44 is turnable via a pivotal support shaft 46. The action portion 44 is disposed in parallel with the probe 24 disposed along an axial direction of the sheath 42. The action portion 44 can be close to and away from an after-mentioned treatment portion 74 of the probe 24, i.e., openable and closable.

It is to be noted that the action portion 44 and the treatment portion 74 of the probe 24 form a grasping portion that grasps the biological tissue.

The operation section 34 is disposed in a proximal portion of the sheath 42. The operation section 34 includes an operation section main body 52, and a movable handle 54 that moves the action portion 44 to be close to and away from the treatment portion 74 of the probe 24. The operation section main body 52 is tabularly formed and its proximal portion is detachably attached to the vibrator unit 26. A central axis of the probe 24, a central axis of the ultrasonic vibrator (an ultrasonic transducer) 62 (see FIG. 5A) of the vibrator unit 26, a central axis of the operation section main body 52, and a central axis of the sheath 42 coincide.

The operation section main body 52 includes a fixed handle 56. The fixed handle 56 extends in a radial direction of the tubular operation section main body 52. The movable handle 54 is supported by the operation section main body 52 to be disposed in parallel with the fixed handle 56. In this embodiment, the movable handle 54 is disposed on a rear side of the fixed handle 56, but the movable handle 54 is also preferably disposed on a front side of the fixed handle 56. Further, by a known mechanism, the movable handle 54 can be made to move close to and away from the fixed handle 56. Consequently, the action portion 44 can be turned to the distal end of the sheath 42.

The operation section 34 includes a rotary knob 58. The rotary knob 58 is present on a front side of the operation section main body 52 and can rotate the sheath 42 and the action portion 44 in a periaxial direction to the probe 24. That is, in a case where the rotary knob 58 is rotated in a periaxial direction to the operation section 34, the rotary knob is integrally rotatable in a periaxial direction to a vibration transmitting portion 72 of the probe 24. Consequently, the action portion 44 pivotally supported by a distal portion of the sheath 42 rotates in the periaxial direction to the probe 24.

The vibrator unit 26 is attachably and detachably disposed in a rear end portion of the operation section main body 52. In the vibrator unit 26 (in a cover 26a), there is received the ultrasonic vibrator (the ultrasonic transducer) 62 (see FIG. 5A) that is preferably, for example, of a BLT type and generates the ultrasonic vibration. A cable 64 is extended from a rear end portion of the vibrator unit 26. A proximal end of the cable 64 is connected to the controller 14 shown in FIG. 1. That is, the ultrasonic vibrator 62 of the ultrasonic vibrator unit 26 is connected to the controller 14 to supply electric power to the ultrasonic vibrator 62. Further, when the power is suitably supplied from an after-mentioned electric power output section 106 of the controller 14 to the ultrasonic vibrator 62, the ultrasonic vibrator 62 is driven to generate the ultrasonic vibration. Consequently, the vibration generated in the ultrasonic vibrator 62 can be transmitted to the probe 24.

The probe 24 shown in FIG. 2, which made of a metal material such as a titanium alloy, is formed into a rod shape. The probe 24 includes the elongated vibration transmitting portion 72 having a horn 72a to enlarge the amplitude, and the treatment portion 74 integrally formed on a distal side of the vibration transmitting portion 72. A proximal end of the vibration transmitting portion 72 is screwed into a distal end of the vibrator unit 26, thereby connecting the probe 24 to the vibrator unit 26. Further, the vibration transmitting portion 72 transmits the ultrasonic vibration generated in the ultrasonic vibrator 62 of the vibrator unit 26 from the proximal end toward the distal end. The vibration transmitting portion 72 transmits the ultrasonic vibration to the treatment portion 74 disposed on its distal side.

A length of the probe 24 is determined by a resonance frequency of the ultrasonic vibrator 62 of the ultrasonic vibrator unit 26. For example, in a case where the resonance frequency of a vertical vibration of the ultrasonic vibrator 62 is 47 kHz, one wavelength is about 100 mm, and hence a space between node positions of the vibration of the probe 24 is about 50 mm. The treatment portion 74 of the probe 24 is present at an antinode position of the vibration and in its vicinity. The resonance frequency of the ultrasonic vibrator 62 is not limited to 47 kHz, and may be 23.5 kHz or the like.

As shown in FIG. 2, in an outer periphery of the vibration transmitting portion 72, holding members 76a, 76b, . . . are disposed away from one another in the axial direction. For example, the holding member 76a is disposed at a position of a node of the ultrasonic vibration of the vibration transmitting portion 72 which is the most distal position. In the case where the resonance frequency of the ultrasonic vibrator 62 is 47 kHz, the holding member 76b is disposed on a rear end side of about 50 mm from the holding member 76a, and hereinafter, the holding members 76c, 76d, . . . are successively disposed via a space of about 50 mm. The holding members 76a, 76b, . . . are made of a ring-shaped rubber material having a non-conductivity (electric insulating properties). The vibration transmitting portion 72 in which the holding members 76a, 76b, . . . are disposed is inserted into the sheath 42. The holding members 76a, 76b, . . . prevent the vibration transmitting portion 72 from coming in contact with an inner peripheral surface of the sheath 42.

Here, as shown in FIG. 1, the treatment portion 74 of the probe 24 projects to the distal end of the sheath 42 on the distal side. Consequently, the action portion 44 faces the treatment portion 74 of the probe 24 to be close to and away from the treatment portion 74.

As shown in FIG. 3A and FIG. 3B, the action portion 44 includes a jaw 82 operated by an operation of the movable handle 54, and a pressing portion 84 that is disposed in the jaw 82, faces the treatment portion 74 of the probe 24, and presses and grasps the biological tissue. As shown in FIG. 3A to FIG. 3C, the pressing portion 84 includes a pad (a buffering portion) 92 made of a resin material such as PTFE having a heat resistance, a wear resistance and a non-conductivity (the electric insulating properties), and a plate 94 made of a metal material such as a vibration damping alloy material disposed in the pad 92 and having the heat resistance and the wear resistance for use as a vibration damping portion. The plate 94 of the metal material for use as the vibration damping portion preferably has a conductivity. The plate 94 is formed to be prevented from being grinded by the probe 24 when abutting on the treatment portion 74 in the state where the ultrasonic vibration is transmitted to the treatment portion 74. Additionally, the plate 94 is formed to be prevented from grinding the probe 24 when abutting on the treatment portion 74 in the state where the ultrasonic vibration is transmitted to the treatment portion 74. That is, the plate 94 has a wear resistance to the probe 24 to which the vibration is transmitted. It is to be noted that the plate 94 preferably has a heat resistance higher than the heat resistance of the pad 92 made of the resin material, and preferably has a wear resistance higher than the wear resistance of the pad 92 made of the resin material.

As shown in FIG. 3B and FIG. 3C, the pressing portion 84 has a distal end 86a, a proximal end 86b and a longitudinal direction L defined by the distal end 86a and the proximal end 86b. The pressing portion 84 has one side 88a, another side 88b and a width direction W defined by the one side 88a and the other side 88b. The longitudinal direction L is preferably orthogonal to the width direction W. Further, the pad 92 of the pressing portion 84 is defined by the longitudinal direction L and the width direction W and forms a grasping surface 96 to grasp the biological tissue in cooperation with the plate 94. The surface (the grasping surface 96) of the pad 92 which faces the treatment portion 74 is, for example, a knurled surface, a satin finished surface or the like, and is preferably formed as a slip stopper to stop the biological tissue slipping.

As shown in FIG. 3A to FIG. 3C, in this embodiment, the plate 94 is substantially disposed in a center of the pressing portion 84 in the longitudinal direction L and the width direction W. As shown in FIG. 3A and FIG. 3B, the surface of the plate 94 is exposed to the outside and is preferably present at a slightly dented position on a back surface side to the surface of the pad 92 (a side close to the jaw 82).

Figure 4A:
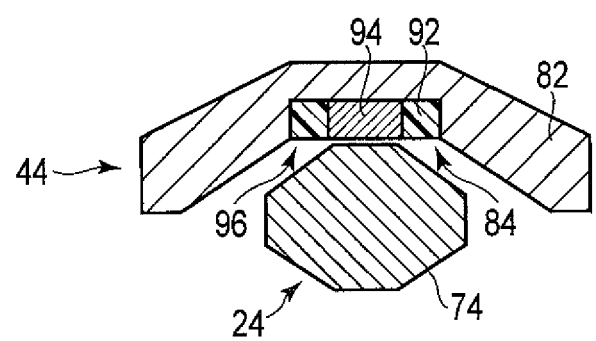
FIG. 4A is a schematic view of a treatment device unit of a treatment system according to a modification of the first embodiment, showing a transverse cross section of an action portion indicating a state of crossing a plate made of a vibration damping alloy material and a state where the surface of the plate is exposed to be flush with the surface of a pad.
Figure 4B:
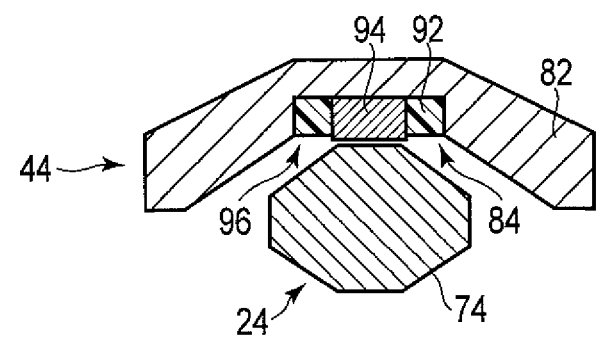
FIG. 4B is a schematic view of the treatment device unit of the treatment system according to the modification of the first embodiment, showing a transverse cross section of the action portion indicating the state of crossing the plate made of the vibration damping alloy material and the state where the surface of the plate is exposed to be flush with the surface of the pad.

It is to be noted that as shown in FIG. 4A, the surface of the plate 94 is preferably exposed to be flush with the surface of the pad 92. Additionally, as shown in FIG. 4B, the surface of the plate 94 is also preferably projected from the surface of the pad 92 to be slightly close to the treatment portion 74.

For the plate 94 made of the vibration damping alloy material for use as the vibration damping portion, as one example, there is preferably used, for example, an iron and aluminum alloy (the Al—Fe alloy) in which a maximum loss coefficient is, for example, about 0.07 and an attenuating capacity is 10% or more. When a vibration damping alloy material is made of Al—Fe, it is preferable to use a material in which an Al content ratio is from about 6 wt. % to 10 wt. % and is especially preferably about 8 wt. %. It is to be noted that in a case where the plate 94 made of the Al—Fe alloy material having an Al content ratio of 8 wt. % is used, the plate 94 has a heat resistance higher than the heat resistance of the pad 92 made of a PTFE material and also has a wear resistance higher than the wear resistance of the pad 92.

The vibration damping alloy material that is the material of the plate 94 has a high rigidity and less deflection amount and less deformation amount, but can absorb the vibration. As the vibration damping alloy material, for example, there is present a member by dislocation, a member by twin crystal deformation, a member by a composite structure, a member by internal friction, a member by any combination of the abovementioned means, or the like. For example, in the case of the member by the dislocation, vibration energy can be absorbed by causing energy loss (the energy loss due to dislocation) in the vibration damping alloy material by interactions of the dislocation and impurities in crystals. In the case of the member by the twin crystal deformation, the vibration energy can be absorbed by causing twin crystal deformation in the vibration damping alloy material.

As the vibration damping alloy material, it is preferable to use a member having, for example, a modulus of elasticity that is not different from that of iron and thus having a strength equal to or higher than that of iron, i.e., an excellent non-strength, but having a specific weight as much as about 10% less than that of iron. As the vibration damping alloy material, it is preferable to use a member that is comparatively easy to be processed by forging, press forming or cutting. As the vibration damping alloy material, it is further preferable to use a member that has an oxidation resistance function due to an oxide coating film stabilized even at a low or high temperature and is resistant to brittle fracture and can be processed into a complex shape at ordinary temperature. The vibration damping alloy material is a metal material and has a conductivity, but its resistance value is preferably, for example, about several times, such as four times, a resistance value of iron.

It is to be noted that as the vibration damping alloy material, in addition to an Al—Fe alloy, there are suitably used, for example, a composite type of Al—Zn alloy, a twin crystal type of Ni—Ti alloy, a Cu—Al—Ni alloy, an Mn—Cu alloy, Mn—Cu—Ni—Fe and the like. In a case where the vibration damping alloy material is used as the plate 94 according to this embodiment, the vibration damping alloy material preferably has an attenuating capacity of 10% or more.

Figure 5A:
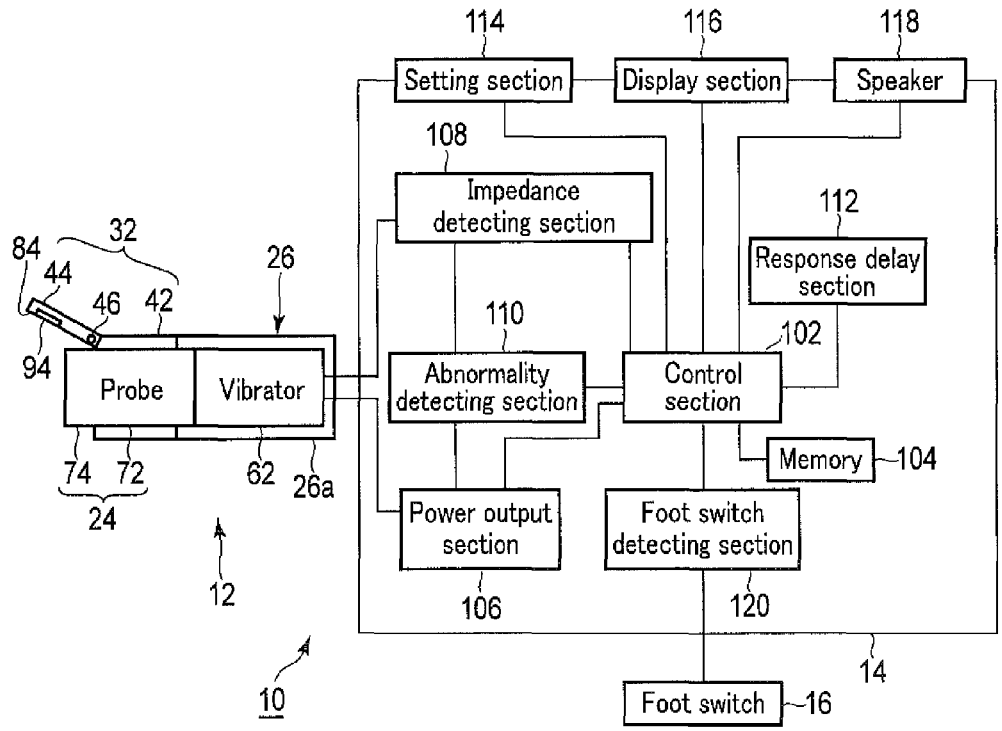
FIG. 5A is a schematic block diagram showing a treatment system according to the first to fifth embodiments.
Figure 5B:
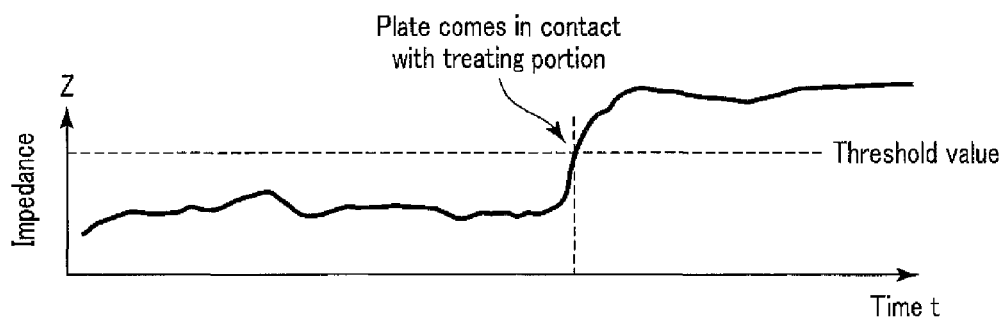
FIG. 5B is a schematic view showing a change of an acoustic impedance of an ultrasonic transducer over time including the time when the plate of the treatment system according to the first embodiment abuts on the treatment portion of the probe to which a vibration is transmitted.

In this embodiment, there will be described an example where the controller 14 executes the constant current control when the ultrasonic vibrator 62 is driven. As shown in FIG. 5A, the controller 14 includes a control section 102, a memory 104, the electric power output section (an AC power source section) 106, an impedance detecting section 108, an abnormality detecting section 110, a response delay section 112, a setting section 114, a display section 116, a speaker 118, and a foot switch detecting section 120. The memory 104, the electric power output section 106, the impedance detecting section 108, the abnormality detecting section 110, the response delay section 112, the setting section 114, the display section 116, the speaker 118 and the foot switch detecting section 120 are connected to the control section 102 to transmit and receive electric signals. The foot switch detecting section 120 detects an operation of a pedal 16a of the foot switch 16.

In the memory 104, a maximum voltage and the like are stored on the basis of values set in the setting section 114, and a threshold value of an impedance detected by the impedance detecting section 108 (see FIG. 5B) and the like are stored.

The electric power output section 106 and the impedance detecting section 108 are connected to the vibrator 62 of the vibrator unit 26. The abnormality detecting section 110 is connected to the power output section 106 and the impedance detecting section 108. The abnormality detecting section 110 can detect an abnormality of an output amount of the power output section 106, an abnormality of a detected value of the impedance detecting section 108, and the like.

In this embodiment, the constant current control is executed, and hence in a case where the amplitude of the treatment portion 74 is kept constant, the voltage is raised with a rise in impedance Z. At this time, the response delay section 112 can delay a rise time of the voltage via a setting in the setting section 114. Consequently, a time until the maximum voltage is reached can be delayed. It is to be noted that by the setting in the setting section 114, the user can prevent the time until the maximum voltage is reached from being delayed.

The user can perform the setting in the setting section 114 so that the electric power is not output to the vibrator 62 when the abnormality detecting section 110 detects, for example, an abnormality in which the probe 24 is not connected or a short circuit occurs in the probe 24, in a case where electric power is output from the power output section 106 to the vibrator 62.

Next, an operation of the treatment system 10 according to this embodiment will be described.

The user attaches the probe 24 and the vibrator unit 26 to the operation unit 22 to form the treatment device unit 12. Further, the vibrator unit 26 is connected to the controller 14. At this time, the plate 94 is disposed in the pressing portion 84 in a state of facing the treatment portion 74 of the probe 24.

The user operates the movable handle 54 of the operation section 34 to move, to be close to the treatment portion 74, the action portion 44 once moved away from the treatment portion 74 of the probe 24, and sandwiches the biological tissue between the treatment portion 74 of the probe 24 and the grasping surface 96 of the pressing portion 84. That is, the user presses the biological tissue toward the treatment portion 74 of the probe 24 with the pressing portion 84.

In this state, the user pushes down the pedal 16a of the foot switch 16 to output the power from the electric power output section 106 to the vibrator 62 of the vibrator unit 26, thereby generating the ultrasonic vibration in the vibrator 62. The ultrasonic vibration generated in the vibrator 62 is transmitted to the treatment portion 74 through the vibration transmitting portion 72 of the probe 24. By the frictional heat between the treatment portion 74 of the probe 24 to which the ultrasonic vibration is transmitted and the biological tissue pressed toward the treatment portion 74 by the action portion 44, the biological tissue can be incised while performing coagulation, i.e., stopping of bleeding. Consequently, the biological tissue pressed toward the treatment portion 74 can be separated in the treatment portion 74 of the probe 24.

The pressing portion 84 presses the biological tissue toward the treatment portion 74 of the probe 24, and hence the grasping surface 96 of the pressing portion 84 comes close to the treatment portion 74 of the probe 24 as the biological tissue is cut and divided by the ultrasonic vibration transmitted to the treatment portion 74 of the probe 24. In a case where the surface of the plate 94 is flush with the surface of the pad 92, when the biological tissue is separated, the plate 94 abuts on the treatment portion 74 of the probe 24. Additionally, in a case where the plate is present at the slightly dented position on the back surface side to the surface of the pad 92 (the side close to the jaw 82) and the surface of the plate 94 is positioned to be abuttable on the treatment portion 74 after the surface of the pad 92 made of the resin material abuts thereon, i.e., the case where the plate is present at the slightly dented position on the back surface side to the surface of the pad 92 (the side close to the jaw 82), when the biological tissue is cut and divided, the pad 92 made of the resin material is elastically deformed to the treatment portion 74, whereby the plate 94 abuts on the treatment portion 74.

When the plate 94 comes in contact with the treatment portion 74 of the probe 24 in a state where the ultrasonic vibration from the ultrasonic vibrator unit 26 is input into the proximal end of the probe 24, the plate 94 follows the vibration of the treatment portion 74 of the probe 24. Consequently, the plate 94 moves to vibrate together with the vibration of the treatment portion 74. That is, when the treatment portion 74 to which the vibration is transmitted abuts on the plate 94, the plate 94 follows the movement of the treatment portion 74. Consequently, there is apparently obtained the same state that the plate 94 is attached to the treatment portion 74. Further, the treatment portion 74 of the probe 24 is prevented from grinding the plate 94, and the plate 94 is also prevented from grinding the treatment portion 74 of the probe 24. Furthermore, the pad 92 of the pressing portion 84 is prevented from being cut. The plate 94 moves together with the vibration of the treatment portion 74, and hence the plate 94 absorbs the vibration energy transmitted to the treatment portion 74, thereby causing energy loss as the ultrasonic vibrator vibrates. In this way, the energy of the vibration is transmitted and absorbed from the treatment portion 74 to the plate 94, and hence a braking operation works on the ultrasonic vibration of the treatment portion 74 of the probe 24. The user can recognize a state where the braking operation works in this way. Therefore, the treatment device unit 12 can stop ultrasonic vibration or prompt the user to stop ultrasonic vibration immediately after the biological tissue is separated in cooperation with the treatment portion 74 of the probe 24 to which the ultrasonic vibration is transmitted.

The plate 94 for use as the vibration damping portion according to this embodiment is made of, for example, the vibration damping alloy material. Thus, the plate 94 is to damp, i.e., attenuate the vibration in accordance with its attenuating capacity earlier than in a case where another metal material such as a stainless steel alloy material of the same shape is used. Therefore, when the energy of the vibration is transmitted from the treatment portion 74 to the plate 94 made of the vibration damping alloy material, the material having high attenuating capacity and high followability is used in the plate 94, and hence the braking operation can work on the ultrasonic vibration of the treatment portion 74 of the probe 24 earlier. That is, the plate 94 can function as the vibration damping portion that damps (attenuates) the ultrasonic vibration of the treatment portion 74 of the probe 24.

It is to be noted that even when the plate 94 made of the vibration damping alloy material according to this embodiment, i.e., the vibration damping alloy material comes in contact with the treatment portion 74 of the probe 24 to which the vibration is transmitted, the vibration damping alloy material follows the movement of the treatment portion 74, and hence the treatment portion 74 of the probe 24 can be prevented from being damaged.

In this way, the user of the treatment system 10 can immediately recognize that the biological tissue is separated by the treatment portion 74 of the probe 24 in a state where the braking operation works on the vibration of the treatment portion 74 of the probe 24, i.e., the vibration is damped, when the plate 94 abuts on the treatment portion 74 of the probe 24. The state that the braking operation works to the vibration of the treatment portion 74 of the probe 24 is the same as a state where the user is prompted to release the pressing of the pedal 16a of the foot switch 16. Therefore, on recognizing that the biological tissue is cut and divided, the user of the treatment system 10 can immediately release the pushdown of the pedal 16a of the foot switch 16 to stop the ultrasonic vibration generated in the ultrasonic vibrator 62. Thus, friction between the treatment portion 74 of the probe 24 to which the vibration is transmitted and the pad 92 made of the resin material can be avoided as much as possible, and wear of the pad 92 made of the resin material can be inhibited as much as possible. Therefore, a life of the pad 92 made of the resin material can noticeably be extended as compared with a case where the ultrasonic vibration is not immediately stopped after the plate 94 abuts on the treatment portion 74 of the probe 24 to which the vibration is transmitted.

Additionally, when the plate 94 abuts on the treatment portion 74 to which the vibration is transmitted, the impedance detecting section 108 of the controller 14 detects the rapid rise of the acoustic impedance Z of the ultrasonic vibrator 62 immediately prior to the abutment. The controller 14 rapidly raises the voltage from the electric power output section 106 to the ultrasonic vibrator 62 to raise the output electric power, and then maintains the amplitude of the treatment portion 74 at a certain level by constant current control.

Here, a threshold value of the acoustic impedance Z is beforehand stored in the memory 104, and when the impedance Z detected by the impedance detecting section 108 is in excess of the maximum impedance (the threshold value), the abnormality detecting section 110 detects this abnormality. Additionally, a voltage (a maximum voltage threshold value) or electric power (a maximum power threshold value) that can be output from the power output section 106 to the ultrasonic vibrator 62 is beforehand stored in the memory 104, and when the output is in excess of the maximum voltage threshold value or the maximum power threshold value, the abnormality detecting section 110 detects this abnormality, and the supply of the power from the power output section 106 to the vibrator 62 is stopped.

In this embodiment, when the plate 94 made of the metal material having the conductivity abuts on the treatment portion 74 to which the vibration is transmitted, the acoustic impedance Z rises. At this time, when the constant current is to be maintained, the output is in excess of the maximum voltage threshold value, and the ultrasonic vibration of the ultrasonic vibrator 62 stops. That is, immediately after the plate 94 abuts on the treatment portion 74 to which the vibration is transmitted, the transmission of the ultrasonic vibration is stopped. The maximum output voltage and the maximum output power that can be output from the power output section 106 to the vibrator 62 are beforehand determined, and hence the ultrasonic vibration is output until the maximum output voltage or the maximum output power is reached, but when the maximum output voltage or the maximum output power is reached, the ultrasonic vibration is forcibly stopped.

In this way, it can be judged that the biological tissue in contact with the treatment portion 74 facing the plate 94 is separated, when the plate 94 abuts on the treatment portion 74 to which the vibration is transmitted. However, in a case where a contact area of the plate 94 to the treatment portion 74 is small, it is not judged whether or not the biological tissue is separated at a position of the treatment portion 74 which is away from its position facing the plate 94. The response delay section 112 of the controller 14 performs adjustment to delay the response time of control of the voltage of the power output section 106 on the basis of a change of the impedance Z, whereby an increase of the acoustic impedance Z of the vibrator 62 is recognized, and then the ultrasonic vibration can continue to be output for a predetermined time of, e.g., several seconds to about ten seconds. As the delay time, a predetermined time of several seconds to about ten seconds or the like is beforehand set in the setting section 114 by the user. Thus, the user suitably sets the response delay section 112 in the setting section 114, thereby delaying the voltage rise of the power output section 106, so that the time until the maximum electric power threshold value is reached can be adjusted. Further, the ultrasonic vibration of the vibrator 62 is prevented from being stopped immediately after the plate 94 abuts on the treatment portion 74 to which the vibration is transmitted, thereby continuing to generate the ultrasonic vibration in the treatment portion 74 for the predetermined time of, e.g., several seconds and the like, so that the biological tissue can completely be separated.

The user beforehand stores, in the memory 104, the threshold value of the impedance Z when the plate 94 made of the vibration damping alloy material abuts on the treatment portion 74 of the probe 24, and a rise amount of the impedance Z per unit time. When the rise of the impedance Z is caused in excess of such a threshold value or rise amount per unit time, the controller 14 can inform the user that the plate 94 made of the vibration damping alloy material abuts on the treatment portion 74 of the probe 24, by a sound from the speaker 118 and/or display of the display section 116 or the like. That is, the user can recognize that at least a part of the biological tissue is cut and divided, by the sound and/or the display or the like.

As described above, this embodiment can be considered as follows.

In the treatment device unit 12, the operation unit (the treatment device) 22 for use as the treatment device in cooperation with the ultrasonic vibrator unit 26 and the probe 24 can cut and divide the biological tissue by use of the ultrasonic vibration. The action portion 44 has the pressing portion 84 that can be close to and away from the treatment portion 74 of the probe 24 in which the ultrasonic vibration is transmittable from the proximal portion thereof toward the distal portion thereof, and which has the treatment portion 74 in the distal portion, so that the biological tissue is pressed and grasped between the pressing portion and the treatment portion 74. Further, the plate 94 as the vibration damping portion has the conductivity, and is disposed in the state of facing the probe 24 in the pressing portion 84 and being exposed to the probe 24. The plate 94 is prevented from being damaged by the probe 24 to which the vibration is transmitted and also prevented from damaging the probe 24. Additionally, the plate 94 moves following the vibration of the probe 24 when abutting on the probe 24 to which the vibration is transmitted, and absorbs the vibration. Further, when the plate 94 abuts on the treatment portion 74 in the state where the ultrasonic vibration is transmitted to the treatment portion 74, the braking operation is given to the treatment portion 74 to which the ultrasonic vibration is transmitted. Consequently, the user can recognize that the biological tissue between the grasping surface 96 of the pressing portion 84 and the treatment portion 74 is separated. Therefore, according to the operation unit 22 of this embodiment, immediately after the biological tissue is separated in cooperation with the treatment portion 74 of the probe 24 to which the vibration is transmitted, it is possible to recognize that the biological tissue is separated, and it is possible to stop the ultrasonic vibration or prompt the stop. Additionally, by use of the plate 94, the vibration to be transmitted to the probe 24 can be prevented from being applied to the jaw 82 through the pad 92.

Further, the plate 94 prevents the wear of the pad 92 made of the resin material from proceeding and can further extend the replacement period of the pad 92 made of the resin material. That is, the life of the operation unit 22 as the treatment device can be extended. Additionally, the user can recognize that the biological tissue is separated, and hence a generation time of the ultrasonic vibration can be minimized, and shortening of surgical operation time can be achieved.

Particularly, in the plate 94, the vibration damping alloy material that can absorb the vibration energy to be transmitted to the treatment portion 74 is used, so that the abovementioned effect can easily be obtained.

Additionally, also in the treatment device unit 12 where the operation unit 22 as the treatment device is combined with the probe 24 which is disposed in the operation unit 22 and to which the ultrasonic vibration is transmitted, similar effects can be obtained.

In addition, also in the treatment device unit 12 in which the operation unit 22, the probe 24 and the ultrasonic vibrator unit 26 are combined, similar effects can be obtained. Further, in the controller 14, there is detected the change of the acoustic impedance Z of the vibration to be transmitted to the probe 24, before the treatment portion 74 of the probe 24 abuts on the plate 94, when the treatment portion abuts thereon, and further, after the treatment portion abuts thereon, whereby it can be detected that the biological tissue between the pressing portion 84 and the treatment portion 74 is separated. Therefore, according to the treatment system 10 of this embodiment, when it is detected that the biological tissue between the pressing portion 84 and the treatment portion 74 is separated, the ultrasonic vibration can automatically be stopped and unnecessary wear of the pad 92 can be prevented.

Additionally, in this embodiment, it has been described that the controller 14 stops the output to the vibrator 62 in accordance with the change of the acoustic impedance Z or stops the output to the vibrator 62 in several seconds after the change of the acoustic impedance Z. In addition, the electric signal including the acoustic impedance Z is also preferably used to stop the output of the vibration to the vibrator 62 as described later in a fourth embodiment.

The controller 14 can control the energy output to the ultrasonic vibrator unit 26 to maintain the amplitude of the treatment portion 74 of the probe 24, on the basis of the change of the impedance Z.

The plate 94 has the heat resistance and the wear resistance to the treatment portion 74 to which the ultrasonic vibration is transmitted. Further, the plate 94 follows the treatment portion 74 to which the ultrasonic vibration is transmitted. Consequently, the plate 94 itself is prevented from being worn as much as possible.

The surface of the plate 94 is preferably positioned to be abuttable on the treatment portion 74 substantially simultaneously when the surface of the pad 92 made of the resin material abuts on the treatment portion, or preferably positioned to be abuttable on the treatment portion 74 after the surface of the pad 92 made of the resin material abuts on the treatment portion. Even in the case where the plate is positioned to be abuttable on the treatment portion 74 after the surface of the pad 92 made of the resin material abuts on the treatment portion, the pad 92 made of the resin material is deformed to the probe 24, so that the treatment portion 74 can abut on the plate 94. It is to be noted that the plate can be positioned to be abuttable on the treatment portion 74 before the surface of the pad 92 made of the resin material abuts on the treatment portion 74.

Figure 6A:
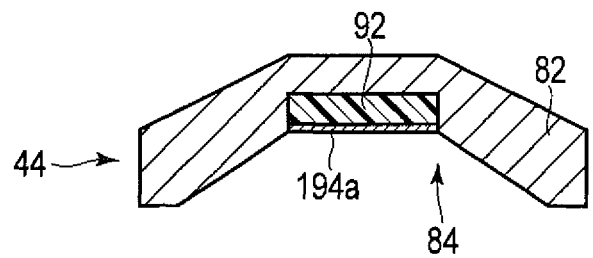
FIG. 6A is a schematic view of a treatment device unit of a treatment system according to another modification of the first embodiment, showing a transverse cross section of an action portion indicating a state of crossing a plate made of a vibration damping alloy material and a state where the surface of a vibration damping alloy material to vibration damping portion) is formed as a thin film on the surface of a pad.

In this embodiment, there has been described the example where the plate-shaped vibration damping alloy material is used as the plate 94, but as shown in FIG. 6A, the pad 92 is also preferably coated with a thin film 194a made of a vibration damping alloy material. Consequently, also when the thin film 194a is disposed on a part of the surface of, e.g., a center of the pad 92, a braking effect can be exerted in the same manner as in the plate 94. The thin film 194a is also preferably formed on the whole surface of the pad 92.

Figure 6B:
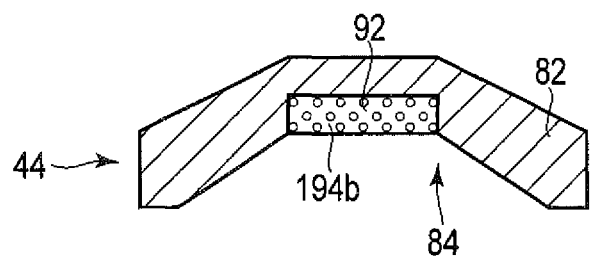
FIG. 6B is a schematic view of a treatment device unit of a treatment system according to still another modification of the first embodiment, showing a transverse cross section of an action portion indicating a state of crossing a plate made of a vibration damping alloy material and a state where a vibration damping alloy material is mixed as powder grains in a pad.

Additionally, as shown in FIG. 6B, it is also preferable to use the pad 92 made of the resin material in which powder grains 194b made of a vibration damping alloy material are mixed. In this way, the powder grains 194b of the vibration damping alloy material are mixed in the pad 92, and hence the braking effect can be exerted in the same manner as in the plate 94. It is to be noted that a density of the powder grains 194b is preferably adjusted to be as high as possible so that the pad surely comes in contact with the treatment portion 74 of the probe 24.

The material used for the vibration damping material of the plate 94 is not limited to an alloy material. A metal material such as an alloy material that is not the vibration damping alloy material of stainless steel or the like is inferior in attenuating capacity to the abovementioned vibration damping alloy material. However, when the plate 94 made of the metal material, e.g., the alloy material that is not the vibration damping alloy material having the wear resistance abuts on the vibrating treatment portion 74, the plate 94 absorbs the vibration energy to be transmitted to the treatment portion 74 and the energy loss is generated. The energy of the vibration is transmitted from the treatment portion 74 to the plate 94 made of the metal material of the alloy material or the like that is not the vibration damping alloy material, so that the braking operation can work on the ultrasonic vibration of the treatment portion 74 of the probe 24.

When the plate 94 of the action portion 44 abuts on the treatment portion 74, the acoustic impedance Z of the vibrator 62 rises. Consequently, when the impedance detecting section 108 detects the impedance Z and the abnormality detecting section 110 can detect the abnormality of the impedance Z, a short circuit may be caused by the plate 94 of the action portion 44 which abuts on the treatment portion 74. When the plate 94 abuts on the treatment portion 74, the abnormality detecting section 110 detects the short circuit, the response delay section 112 is controlled to generate the ultrasonic vibration for several seconds to several tens of seconds, and then the vibration can be stopped.

It is to be noted that in this embodiment, there has been described the example where the treatment is performed by using the ultrasonic vibration, but as described in an aftermentioned third embodiment, needless to say, a treatment of a biological tissue may suitably be performed by combining high frequency energy with the ultrasonic vibration energy.

Next, a second embodiment will be described with reference to FIG. 7. This embodiment is a modification of the first embodiment, and the same members as the members described in the first embodiment are denoted with the same reference signs, and detailed description thereof is omitted.

Figure 7:
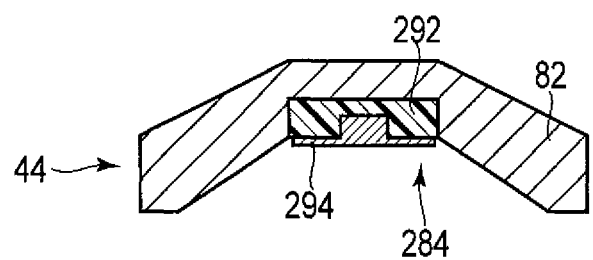
FIG. 7 is a schematic transverse cross section showing a state where an action portion of a treatment device unit of a treatment system according to the second embodiment has a buffering portion made of a resin material and a plate made of a metal material, and the plate is positioned to be abuttable on a treatment portion prior to the surface of the buffering portion made of the resin material.

As shown in FIG. 7, a pressing portion 284 of the action portion 44 includes the jaw 82, a pad (a buffering portion) 292 made of a resin material, and a plate 294 made of a metal material. The pad 292 is made of, for example, a PTFE material or the like in the same manner as in the pad 92 described in the first embodiment.

The plate 294 according to this embodiment is positioned to be abuttable on the treatment portion 74 of the probe 24 prior to the surface of the pad 292. That is, the surface of the plate 294 projects from the surface of the pad 292 to the treatment portion 74 of the probe 24. The plate 294 according to this embodiment may be disposed on a part of the surface of the pad 292 or may be disposed on the whole surface thereof as in the plate 94 described in the first embodiment. It is to be noted that when the plate 294 is disposed on the whole surface of the pad 292, the pad 292 is not exposed to the treatment portion 74 and does not abut on the treatment portion 74 of the probe 24.

As described in the first embodiment, the plate 294 is preferably made of a vibration damping alloy material, but a metal material is also suitably usable.

Even when the plate in the form of a flat surface made of the metal material is to be adhered onto, for example, the PTFE material, it is difficult to bond the plate. In the plate 294 according to this embodiment, a transverse cross section is substantially formed into a T-shape. Further, a vertical rod part of a letter "T" is driven into the pad 292 made of the resin material. At this time, needless to say, an adhesive is preferably used. The plate 294 according to this embodiment is formed in this manner, and hence the plate 294 can firmly be fixed to the pad 292.

Next, a third embodiment will be described with reference to FIG. 8 to FIG. 9C. This embodiment is a modification of the first and second embodiments, the same members as the members described in the first and second embodiments are denoted with the same reference signs, and a detailed description is omitted.

Figure 8:
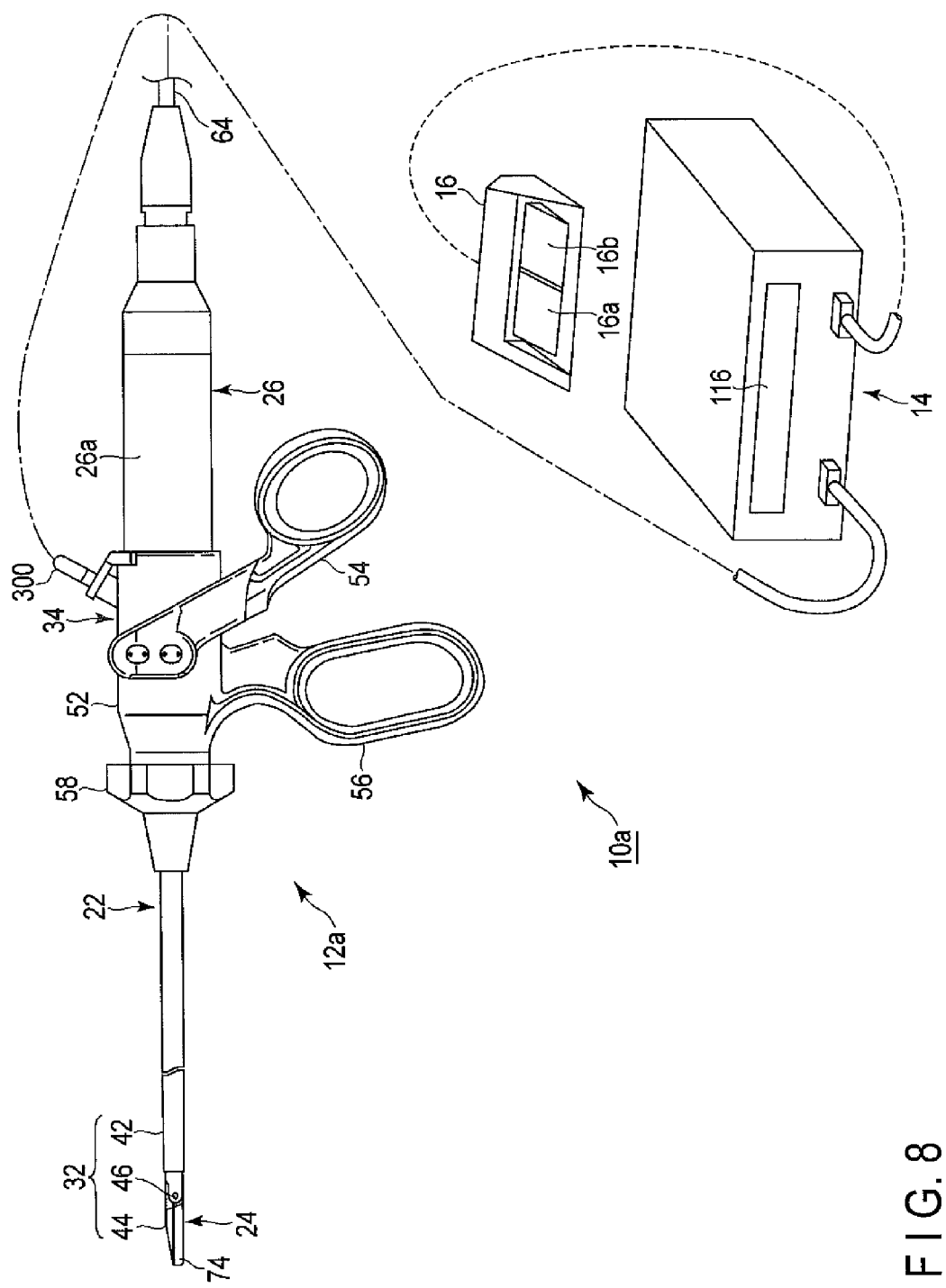
FIG. 8 is a schematic view showing a treatment system according to the third embodiment.
Figure 9A:
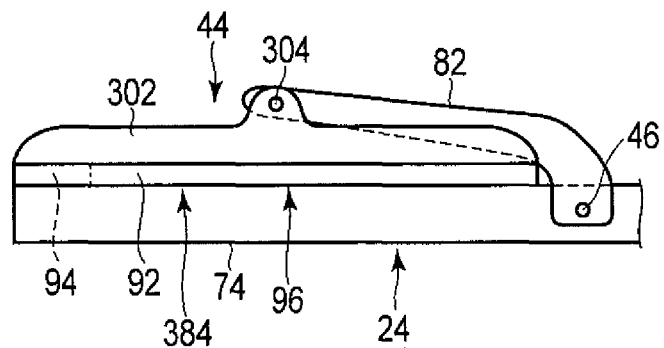
FIG. 9A is a schematic side view of a treatment device unit of the treatment system according to the third embodiment, showing an action portion and a treatment portion of a probe.
Figure 9B:
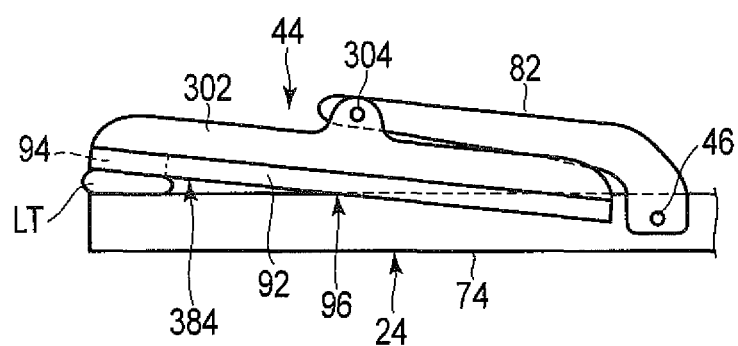
FIG. 9B is a schematic side view of the treatment device unit of the treatment system according to the third embodiment, showing a state where a biological tissue is grasped with the action portion and a distal end of the treatment portion of the probe.

As shown in FIG. 8, in the operation section main body 52 of the operation unit 22 of a treatment device unit 12a of a treatment system 10a according to this embodiment, a pin 300 electrically connected to the probe 24 is disposed. As shown in FIG. 9A to FIG. 9C, in this embodiment, the plate 94 is disposed at a distal end of the pad (a buffering portion) 92. As shown in FIG. 3A and FIG. 3B, the surface of the plate 94 may be close to the jaw 82 to the surface of the pad 92, but is also preferably flush with the surface of the pad 92. The plate 94 has a conductivity, and hence the treatment portion 74 of the probe 24 and the plate 94 also function as high frequency electrodes, respectively. It is to be noted that in a foot switch 16, in addition to a pedal 16a to output power that generates an ultrasonic vibration, another pedal 16b to output high frequency energy is disposed. Although not shown in the drawings, the controller 14 has a high frequency energy output section to be controlled by the control section 102 shown in FIG. 5A. The high frequency energy output section is preferably disposed in parallel with the electric power output section 106. It is to be noted that by pressing down, for example, both the pedals 16a and 16b, it is possible to output the high frequency energy while outputting ultrasonic energy.

As described in the first embodiment, a biological tissue can be incised while being coagulated, by vibrating the treatment portion 74 of the probe 24. The high frequency energy is applied to the biological tissue between the treatment portion 74 of the probe 24 as a first electrode and the plate 94 as a second electrode, so that a bleeding stopping treatment of the biological tissue can be performed. Therefore, by simultaneously outputting the ultrasonic vibration energy and the high frequency energy, the biological tissue can more easily be cut and divided while enhancing a bleeding stopping capability.

A user of the treatment system 10a according to this embodiment can immediately recognize that the biological tissue is separated by the probe 24a in a state where the braking operation works to reduce the vibration of the treatment portion 74 of the probe 24, i.e., the vibration is damped, when the plate 94 abuts on the treatment portion 74 of the probe 24.

Therefore, according to the operation unit 22 of this embodiment, immediately after the biological tissue is separated in cooperation with the treatment portion 74 of the probe 24 to which the vibration is transmitted, it is possible to detect that the biological tissue is separated, and it is possible to stop the ultrasonic vibration or prompt the user to stop the vibration.

Additionally, also in the treatment device unit 12 where the operation unit 22 as the treatment device is combined with the probe 24 which is disposed in the operation unit 22 and to which the ultrasonic vibration is transmitted, similar effects can be obtained. Additionally, also in the treatment device unit 12 in which the operation unit 22, the probe 24 and the ultrasonic vibrator unit 26 are combined, similar effects can be obtained. Furthermore, according to the treatment system 10a of this embodiment, when it is detected that the biological tissue between an after-mentioned pressing portion 384 and the treatment portion 74 is cut and divided, the ultrasonic vibration can automatically be stopped and unnecessary wear of the pad 92 can be prevented.

Figure 9C:
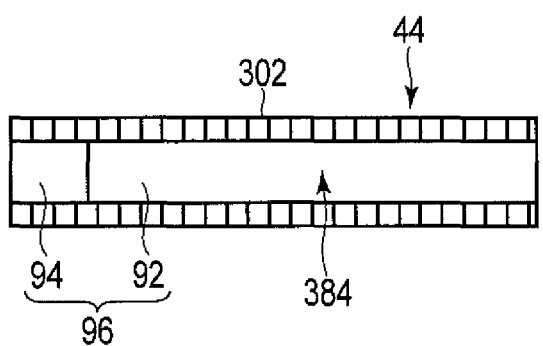
FIG. 9C is a schematic front view of the treatment device unit of the treatment system according to the third embodiment, showing a grasping portion in which a plate made of a vibration damping alloy material is disposed at a distal end in a longitudinal direction and a width direction.

As shown in FIG. 9A to FIG. 9C, the action portion 44 according to this embodiment includes the jaw 82, and a swinging member 302 supported by a supporting portion 304 to be turnable to the jaw 82. In the swinging member 302, there are disposed the pad 92 made of a resin material and the plate 94 made of a vibration damping alloy material. The swinging member 302, the pad 92 and the plate 94 function as the pressing portion 384 that presses the biological tissue in the same manner as in the pressing portion 84 described in the first embodiment. In the action portion 44, the swinging member 302 is formed as a so-called seesaw jaw that turns like a seesaw of play equipment. Further, the swinging member 302 can substantially uniformly apply a holding pressure to the biological tissue via the pad 92.

It is to be noted that in this embodiment, there has been described the example where the pad 92 and the plate 94 described in the first embodiment are used, but there may be used the pad (the buffering portion made of the resin material) 292 and the plate 294 described in the second embodiment.

Next, a fourth embodiment will be described with reference to FIG. 10A to FIG. 11. This embodiment is a modification of the first to third embodiments, the same members as the members described in the first to third embodiments are denoted with the same reference signs, and detailed description is omitted.

Figure 10A:
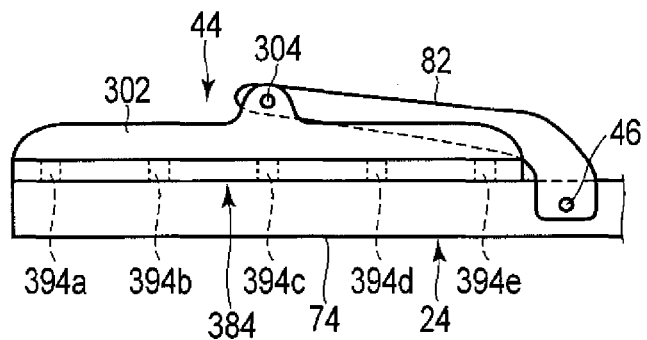
FIG. 10A is a schematic side view showing an action portion of a treatment device unit of a treatment system according to the fourth embodiment.
Figure 10B:
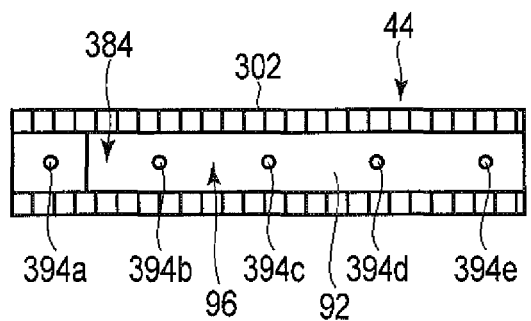
FIG. 10B is a schematic front view of the treatment device unit of the treatment system according to the fourth embodiment, showing a grasping portion in which vibration damping portions made of a vibration damping alloy material are disposed via a suitable space.
Figure 11:
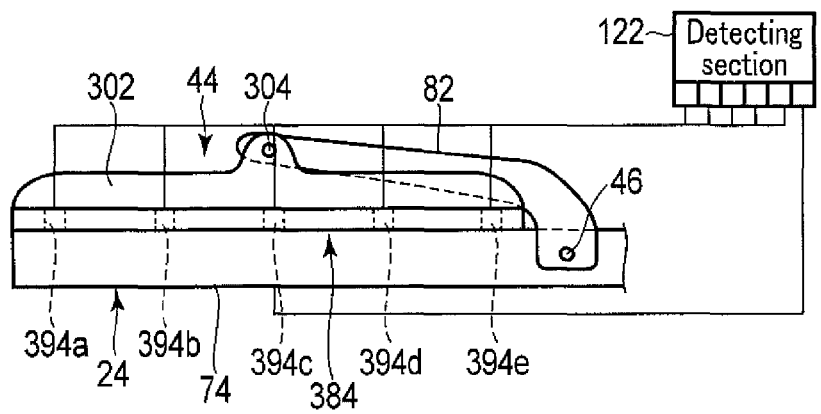
FIG. 11 is a schematic side view showing an action portion of a treatment device unit of a treatment system according to a modification of the fourth embodiment.

As shown in FIG. 10A to FIG. 11, in the pad 92 made of a resin material, five or plural vibration damping members 394a, 394b, 394c, 394d and 394e are disposed in this embodiment. In this embodiment, the vibration damping members 394a, 394b, 394c, 394d and 394e are formed into a pin shape, and one end of each member is exposed to the grasping surface 96. It is to be noted that the other ends of the vibration damping members 394a, 394b, 394c, 394d and 394e are present in a swinging member 302 or at positions close to the swinging member 302. The vibration damping members 394a, 394b, 394c, 394d and 394e are discretely disposed along a longitudinal direction L in this embodiment. The vibration damping members 394a, 394b, 394c, 394d and 394e are preferably disposed via a suitable space. Consequently, when a probe 24 to which a vibration is transmitted abuts on at least one of the vibration damping members 394a, 394b, 394c, 394d and 394e, a braking operation can be exerted as described in the first embodiment.

It is to be noted that the number and spacing of the vibration damping members can suitably be set.

Additionally, as shown in FIG. 11, the controller 14 shown in FIG. 5 preferably includes the detecting section 122 connected to the control section 102. The respective vibration damping members 394a, 394b, 394c, 394d and 394e are electrically connected to the detecting section 122. The detecting section 122 is electrically connected to the probe 24. Consequently, the detecting section 122 detects, for example, an impedance Z between the probe 24 and each of the vibration damping members 394a, 394b, 394c, 394d and 394e, so that the vibration damping member that comes in contact with the probe 24 can be detected in the vibration damping members 394a, 394b, 394c, 394d and 394e. That is, the vibration damping member that comes in contact with a treatment portion 74 of the probe 24 in the vibration damping members 394a, 394b, 394c, 394d and 394e outputs an electric signal toward the detecting section 122, to judge whether a biological tissue in the vicinity of each vibration damping member is separated.

Further, when the detecting section 122 detects that all the vibration damping members 394a, 394b, 394c, 394d and 394e abut on the treatment portion 74, a controller 14 preferably executes control to judge that the biological tissue is completely separated. The controller 14 preferably executes control to automatically stop, for example, an output to an ultrasonic vibrator 62, when the detecting section 122 detects that all the vibration damping members 394a, 394b, 394c, 394d and 394e abut on the treatment portion 74. The controller 14 also preferably executes control to automatically stop the output to the ultrasonic vibrator 62 when one or more of the vibration damping members 394a, 394b, 394c, 394d and 394e abuts on the treatment portion 74. For example, the setting section 114 can suitably set the number of the vibration damping members in the vibration damping members 394a, 394b, 394c, 394d and 394e which abut on the treatment portion 74 to automatically stop the output to the ultrasonic vibrator 62.

Next, a fifth embodiment will be described with reference to FIG. 12 to FIG. 13B. This embodiment is a modification of the first to fourth embodiments, the same members as the members described in the first to fourth embodiments are denoted with the same reference signs, and detailed descriptions thereof are omitted. There will be described an example where a treatment system 10b according to this embodiment can output ultrasonic vibration energy, but both the ultrasonic vibration energy and high frequency energy can simultaneously be output.

Figure 12:
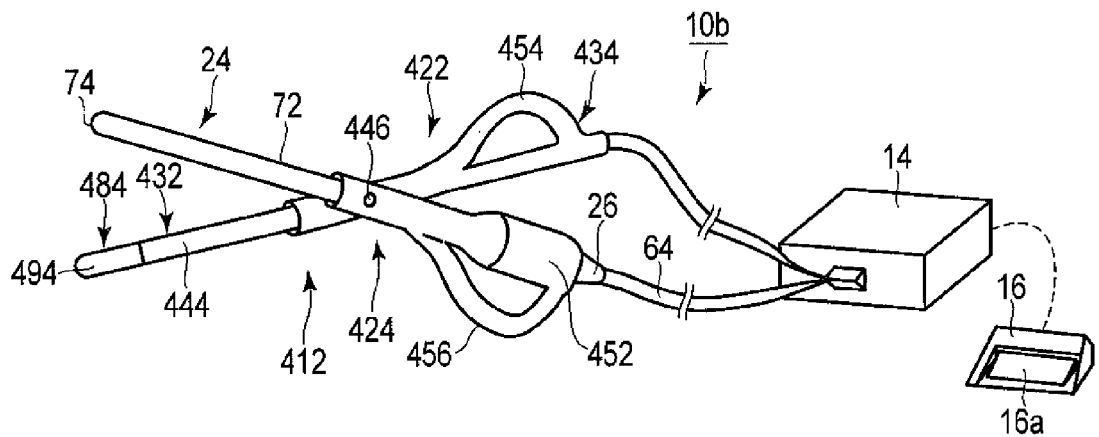
FIG. 12 is a schematic view showing a treatment system according to the fifth embodiment.

As shown in FIG. 12, a treatment device unit 412 according to this embodiment is formed as a scissors type. Consequently, the treatment portion 74 and a pressing portion 484 can apply a shearing force to cut a biological tissue.

The treatment device unit 412 according to this embodiment includes an operation unit 422 and a probe unit 424 having the probe 24 as treatment devices that can be assembled with and disassembled from each other. The probe unit 424 is supported by a supporting portion 446 to be turnable to the operation unit 422. The treatment device unit 412 further includes a vibrator unit 26. A rear end portion of the probe unit 424 is connected to the vibrator unit 26.

The operation unit 422 of the treatment device unit 412 includes an insertion section 432 and an operation section 434. The insertion section 432 includes an action portion (a movable member) 444. The action portion 444 is disposed on a distal side from the supporting portion 446. The action portion 444 is disposed in parallel with the probe 24. The action portion 444 can be close to and away from the treatment portion 74 of the probe 24, i.e., openable and closable.

In a proximal portion of the action portion 444, the operation section 434 is disposed. The operation section 434 has, for example, a first movable handle 454 on which a thumb is placed to move the action portion 444 to be close to and away from the treatment portion 74 of the probe 24.

The probe unit 424 includes, in its proximal portion, for example, a second movable handle 456 on which fingers other than the thumb are placed, and a holder 452 on which the vibrator unit 26 is disposed.

It is to be noted that the first and second holding members 454 and 456 are coated with a material having insulating properties.

The action portion 444 includes a vibration damping portion 494 made of a metal material such as a vibration damping alloy material having a heat resistance, a wear resistance and a conductivity. The vibration damping portion 494 is preferably made of the vibration damping alloy material as described in the first embodiment, has a high rigidity, and has low deflection and low deformation, but can absorb vibration. Further, the vibration damping portion 494 is electrically connected to the controller 14 shown in FIG. 1 and FIG. 5A.

Figure 13A:
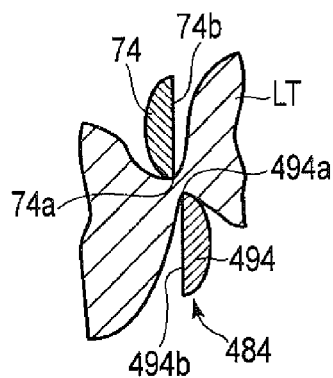
FIG. 13A is a schematic view of a treatment device unit of the treatment system according to the fifth embodiment, showing a state where with a vibration damping portion of an action portion, a biological tissue is pressed to a treatment portion of a probe to apply a shearing force to the biological tissue.
Figure 13B:
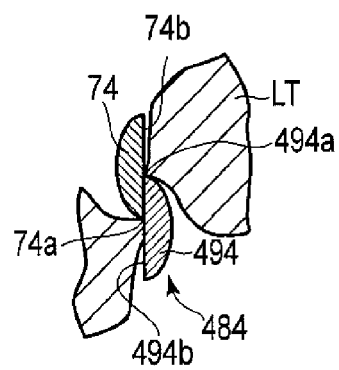
FIG. 13B is a schematic view of the treatment device unit of the treatment system according to the fifth embodiment, showing a state where the vibration damping portion of the action portion abuts on the treatment portion of the probe immediately after the biological tissue is cut by pressing the biological tissue to the treatment portion of the probe to which a vibration is transmitted with the vibration damping portion of the action portion to apply the shearing force to the biological tissue.

As shown in FIG. 13A and FIG. 13B, the treatment portion 74 of the probe 24 and the vibration damping portion 494 disposed in the pressing portion 484 of the action portion 444 have blade portions 74a and 494a, respectively, which abut on the biological tissue when the biological tissue is cut and divided. The treatment portion 74 and the pressing portion 484 of the action portion 444 according to this embodiment have mutually slidable flat surfaces 74b and 494b adjacent to the blade portions 74a and 494a.

Next, an operation of the treatment system 10b according to this embodiment will be described.

In a state where the first and second holding members 454 and 456 are held in one hand of a user, like holding scissors of the stationery products, the biological tissue is sandwiched between the treatment portion 74 of the probe 24 and the pressing portion 484 of the action portion 444. In this state, a pedal 16a of a foot switch 16 is pushed downward to generate an ultrasonic vibration, thereby vibrating the treatment portion 74.

The biological tissue is pressed down toward the blade portion 74a of the treatment portion 74 of the probe 24 with the blade portion 494a of the vibration damping portion 494 disposed in the pressing portion 484 of the action portion 444. The biological tissue can be cut and divided by frictional heat due to the ultrasonic vibration transmitted to the probe 24. Immediately after the biological tissue is separated, the blade portions 74a and 494a come in contact with each other. The vibration damping portion 494 including the blade portion 494a is made of a vibration damping alloy material, and hence, as described in the first embodiment, the vibration damping portion is to attenuate the vibration in accordance with an attenuating capacity earlier than another metal material such as a stainless steel alloy material of the same shape. Further, the vibration damping portion 494 made of a vibration damping alloy material moves together with the vibration of the treatment portion 74, and hence energy loss is generated while the ultrasonic vibrator vibrates. In other words, the vibration damping portion 494 made of the vibration damping alloy material absorbs vibration energy to be transmitted to the treatment portion 74. Consequently, the energy of the vibration is transmitted from the treatment portion 74 to the vibration damping portion 494 made of the vibration damping alloy material, and a braking operation works on the ultrasonic vibration of the treatment portion 74 of the probe 24.

In this way, the user of the treatment system 10b can immediately recognize that the biological tissue is separated by the probe 24 in a state where the braking operation works on the vibration of the treatment portion 74 of the probe 24, i.e., the vibration is damped, when the vibration damping portion 494 abuts on the treatment portion 74 of the probe 24. The state that the braking operation works to the vibration of the treatment portion 74 of the probe 24 is the same as a state where the user is prompted to release the pressing of the pedal 16a of the foot switch 16. Therefore, the user of the treatment system 10b can release the pressure on the pedal 16a of the foot switch 16 to immediately stop the ultrasonic vibration generated in an ultrasonic vibrator 62.

Therefore, according to the operation unit 422 of this embodiment, immediately after the biological tissue is cut and divided in cooperation with the treatment portion 74 of the probe 24 to which the vibration is transmitted, it is possible to detect that the biological tissue is cut and divided, and it is possible to stop the ultrasonic vibration or prompt the stop. It can be recognized by the user that the biological tissue is separated, and hence a generation time of the ultrasonic vibration can be minimized, and shortening of surgical operation time can be achieved.

Figure 14:
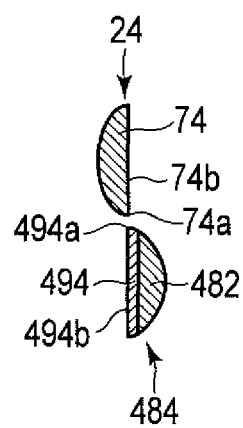
FIG. 14 is a schematic view of a treatment device unit of a treatment system according to a first modification of the fifth embodiment, showing a state where a shearing force can be applied to a biological tissue by pressing the biological tissue to a treatment portion of a probe with a vibration damping portion of an action portion.

It is to be noted that as shown in FIG. 14, the pressing portion 484 of the action portion 444 also preferably includes the vibration damping portion 494 made of the damping alloy material, and a holding portion 482 that holds the vibration damping portion 494.

For example, a material having a rigidity higher than that of the vibration damping portion 494 is used in the holding portion 482, so that the rigidity of the action portion 444 can be adjusted.

Figure 15:
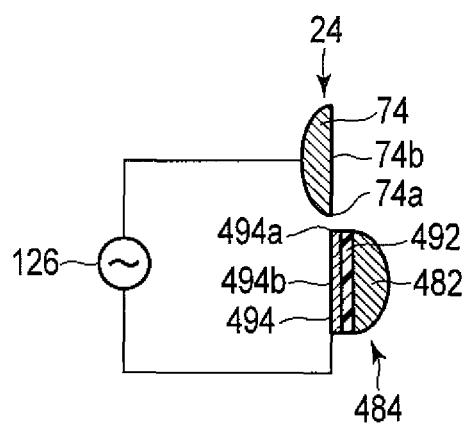
FIG. 15 is a schematic view of a treatment device unit of a treatment system according to a second modification of the fifth embodiment, showing a state where a shearing force can be applied to a biological tissue and high frequency energy can be applied to the biological tissue by pressing the biological tissue to a treatment portion of a probe with a vibration damping portion of an action portion.

As shown in FIG. 15, the pressing portion 484 of the action portion 444 includes the vibration damping portion 494 made of the vibration damping alloy material, an insulating portion 492 having electric insulating properties, and the holding portion 482 that holds the insulating portion 492. The vibration damping portion 494 and the holding portion 482 are electrically insulated. It is to be noted that the probe 24 is defined as a first electrode and the vibration damping portion 494 is defined as a second electrode.

As described in the third embodiment, a high frequency current can be passed through the biological tissue between the treatment portion 74 of the probe 24 as the first electrode and the vibration damping portion 494 as the second electrode, from a high frequency energy output section 126 preferably disposed in parallel with the power output section 106. At this time, the ultrasonic vibration is transmitted to the treatment portion 74 of the probe 24 while applying the high frequency energy to the biological tissue, so that the biological tissue can securely be incised while inhibiting bleeding from the biological tissue, as compared with a case where only the ultrasonic vibration is transmitted.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A treatment device comprising:
   a probe having a distal portion and a proximal portion, and that is configured to connect with an ultrasonic transducer and transmit an ultrasonic vibration generated by the ultrasonic transducer from the proximal portion of the probe to the distal portion of the probe;
   a jaw configured to open and close against the distal portion of the probe;
   a pad attached to the jaw and made of a resin material, the pad being configured to clamp a biological tissue between the pad and the distal portion of the probe; and
   a conductive plate disposed in the pad so that the conductive plate contacts the distal portion of the probe when the jaw is closed against the distal portion of the probe and the biological tissue is separated, the conductive plate having a heat resistance higher than that of the pad and a wear resistance higher than that of the pad.

2. The treatment device according to claim 1, wherein the treatment device is configured to:
   output an electric signal to a controller in a state in which the ultrasonic transducer transmits the ultrasonic vibration to the distal portion of the probe, and
   receive a control signal for changing a vibration state of the probe in response to detecting by the controller that an intensity of the electric signal exceeds a threshold value when the conductive plate contacts the distal portion of the probe under transmission of the ultrasonic vibration.

3. The treatment device according to claim 1, wherein when the conductive plate contacts the distal portion of the probe in the state where the ultrasonic vibration is transmitted to the distal portion of the probe, the conductive plate is prevented from grinding the distal portion of the probe to which the ultrasonic vibration is transmitted.

4. The treatment device according to claim 1, wherein the conductive plate uses a vibration damping alloy member that gives a braking operation of the vibration to the distal portion of the probe to which the ultrasonic vibration is transmitted and absorbs vibration energy to be transmitted to the distal portion of the probe, when the conductive plate contacts the distal portion of the probe in the state where the ultrasonic vibration is transmitted to the distal portion of the probe.

5. The treatment device according to claim 1, wherein the conductive plate raises an acoustic impedance of the ultrasonic transducer immediately before contacting the distal portion of the probe, in the state where the ultrasonic vibration is transmitted to the distal portion of the probe.

6. The treatment device according to claim 1, wherein the conductive plate is disposed in the pad so that, when the jaw is closed against the distal portion of the probe and the biological tissue is separated, a surface of the conductive plate contacts the distal portion of the probe before a surface of the pad contacts the distal portion of the probe.

7. The treatment device according to claim 1, wherein the conductive plate is disposed in the pad so that a surface of the conductive plate and a surface of the pad contact the distal portion of the probe substantially simultaneously when the jaw is closed against the distal portion of the probe and the biological tissue is separated.

8. The treatment device according to claim 1, wherein the conductive plate is disposed in the pad so that, when the jaw is closed against the distal portion of the probe and the biological tissue is separated, a surface of the conductive plate contacts the distal portion of the probe after a surface of the pad contacts the distal portion of the probe.

9. The treatment device according to claim 1, wherein:
   the pad has a distal end, a proximal end, and a longitudinal direction defined by the distal end and the proximal end, and
   the conductive plate is disposed on a side closer to the distal end than a center of the pad between the distal end and the proximal end in the longitudinal direction.

10. The treatment device according to claim 1, wherein:
    the pad has a distal end, a proximal end, and a longitudinal direction defined by the distal end and the proximal end, and
    the conductive plate is disposed in a center of the pad between the distal end and the proximal end in the longitudinal direction.

11. The treatment device according to claim 1, wherein the pad is configured to apply, to the biological tissue, a shearing force that cuts the biological tissue in cooperation with the distal portion of the probe.

12. A treatment device unit comprising:
    the treatment device according to claim 1; and
    a vibrator unit having an ultrasonic transducer that generates an ultrasonic vibration when electric power is supplied to the ultrasonic transducer.

13. A treatment system comprising:
    the treatment device according to claim 1;
    an ultrasonic vibrator unit having an ultrasonic transducer disposed in the treatment device and configured to output an ultrasonic vibration; and
    a controller that is electrically connected to the conductive plate of the treatment device, the ultrasonic transducer and the probe, controls an energy output to the ultrasonic transducer to drive the ultrasonic transducer, is configured to generate the ultrasonic vibration in the probe, and detects, as an electric signal, a change of an acoustic impedance of the ultrasonic transducer when the distal portion of the probe contacts the conductive plate in a state where the ultrasonic transducer is driven to transmit the ultrasonic vibration to the probe, and the controller judging that the biological tissue between the conductive plate and the distal portion of the probe is separated.

14. The treatment system according to claim 13, wherein the controller is configured to control the energy output to the ultrasonic transducer to maintain amplitude of the distal portion of the probe, on the basis of the change of the acoustic impedance.

* * * * *